United States Patent [19]

Baier

[11] 4,233,404
[45] Nov. 11, 1980

[54] METHOD FOR TESTING FOR THE PRESENCE OF PATHOGENS

[75] Inventor: Robert E. Baier, Buffalo, N.Y.

[73] Assignee: Calspan Corporation, Buffalo, N.Y.

[21] Appl. No.: 92,796

[22] Filed: Nov. 9, 1979

[51] Int. Cl.³ .............................................. C12Q 1/24
[52] U.S. Cl. .................... 435/30; 23/230 R; 435/261; 435/292; 435/803
[58] Field of Search .............. 23/230 R; 435/30, 261, 435/292, 803; 55/383, 228

[56] References Cited

U.S. PATENT DOCUMENTS

| 1,893,411 | 1/1933 | Hallerman | 435/803 X |
| 2,871,695 | 2/1959 | Goetz | 435/30 X |
| 3,713,987 | 1/1973 | Low | 435/30 X |

Primary Examiner—Arnold Turk
Attorney, Agent, or Firm—Allen J. Jaffe; David J. Zobkiw

[57] ABSTRACT

Water and air are tested for biological agents by concentrating the biological substances at an air/water interface which permits natural cell multiplication during the concentrating process.

3 Claims, 4 Drawing Figures

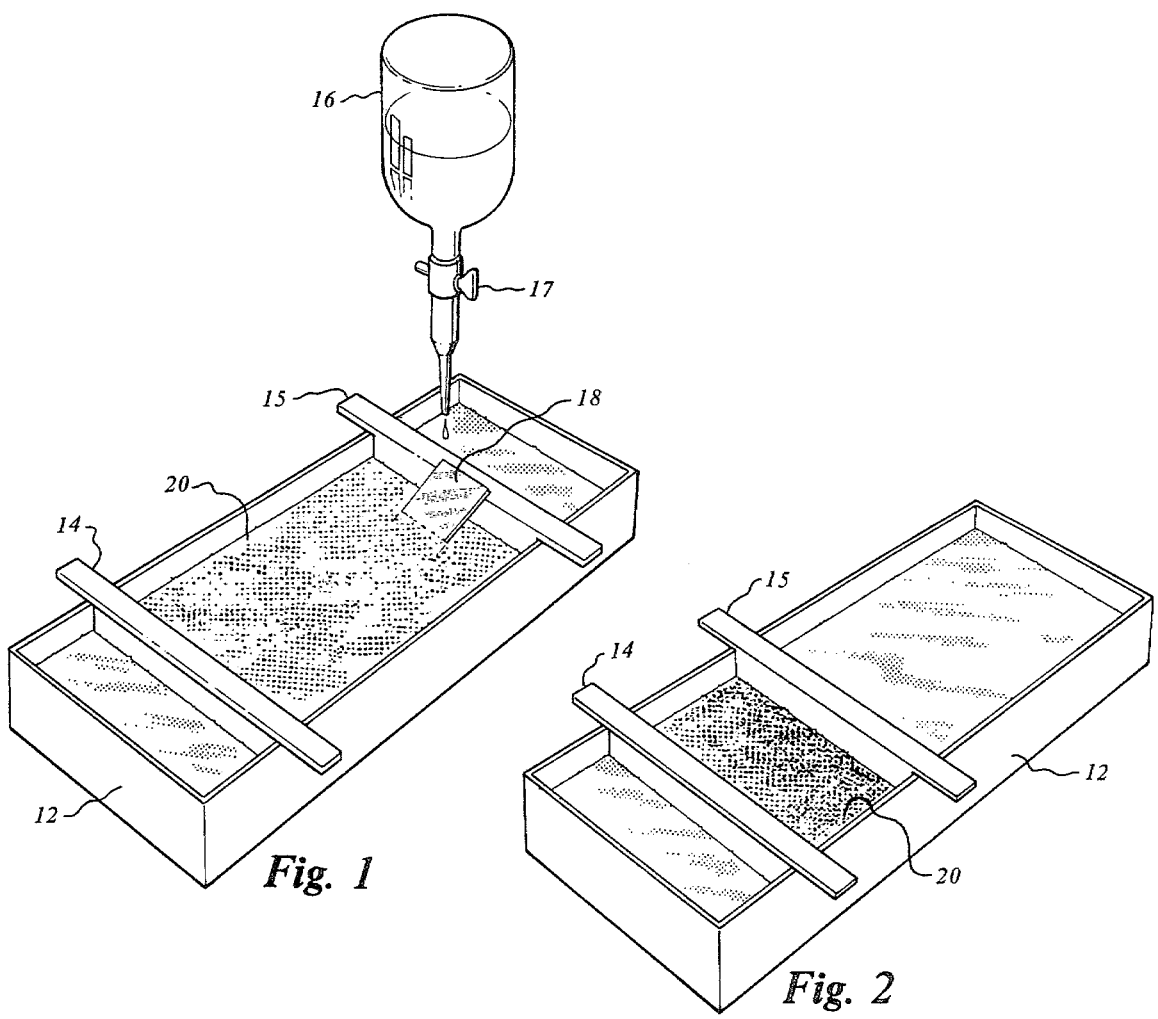
Fig. 1
Fig. 2
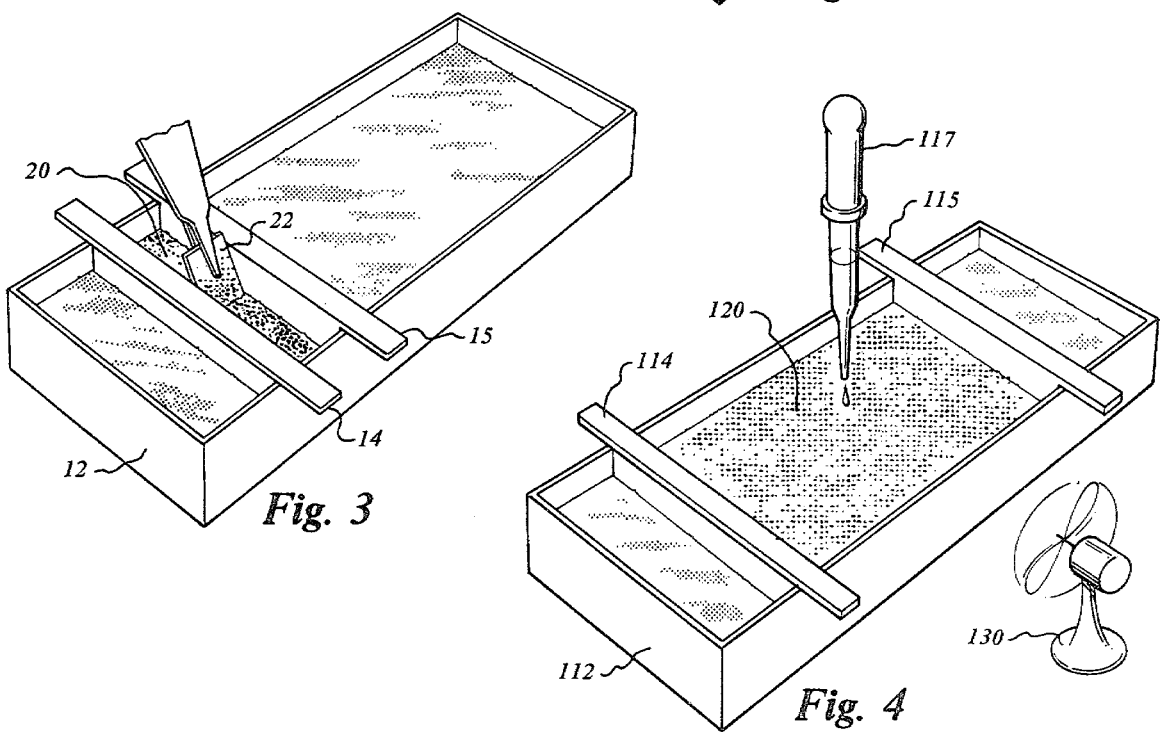
Fig. 3
Fig. 4

METHOD FOR TESTING FOR THE PRESENCE OF PATHOGENS

Biological agents present in water supplies or as airborne microorganisms are typically present in very low concentrations. As a result, it has been standard procedure to incubate samples for periods of about 24 hours in order for the dilute samples to concentrate via cell division. However, in hospitals, first aid areas and similar regions troubled by massive infection distributed by airborne microorganisms from diseased patients to the non-diseased personnel, in biological warfare situations, etc. it is necessary to identify biological pollutants as quickly as possible.

Air sampling devices presently used suffer from a number of deficiencies: they require power, they generate noise, they are bulky and not easily stored, they are expensive, they are inefficient for very small organisms and require a multiplication technique (such as culturing into colonies on good substrates) in the laboratory prior to bacteriological analyses. Air samplers presently available do not lend themselves to multiple coverage of an area, nor to usage by unskilled personnel.

It is an object of this invention to provide a method for concentrating biological agents.

It is a further object of this invention to provide a method for producing a small highly-concentrated biological substance from a dilute sample.

It is an additional object of this invention to provide a method for causing biological agents to concentrate at an air/water interface.

It is a still further object of this invention to provide a method for concentrating waterborne or airborne biological agents.

It is a yet still further object of this invention to provide a rapid test for pathogens.

It is an additional object of this invention to make maximum use of biota actually present in a sample by using a large initial sample volume and concentrating the biological substances at an air/water interface. These objects, and others as will become apparent hereinafter, are accomplished by the present invention.

It is a peculiar and useful property of biological materials that they concentrate preferentially at interfaces. Further, once localized at an interface, biological materials (generally macromolecules) are no longer in equilibrium with material in the bulk phases, and cannot be resolubilized by application of a severe stress (such as the increase in equivalent pressure associated with compression of the film). Instead, the accumulated surface concentrate collapses into an insoluble curd (or fiber) which is even more concentrated and easily removed from the surface.

Basically, according to the present invention, a relatively large air/water interface is provided which serves as a concentrating area for the biological substances contained in an air or water sample. After a sufficient time period, the air/water interface is reduced in area causing the formation of a concentrated sample of the biological substances which can then be removed for analysis.

BRIEF DESCRIPTION OF THE DRAWINGS

For a fuller understanding of the present invention, reference should now be made to the following detailed description thereof taken in conjunction with the accompanying drawings wherein:

FIG. 1 is a pictorial view of a typical field kit for concentrating waterborne pathogens;

FIG. 2 shows the step of skimming the film;

FIG. 3 shows the step of recovering the concentrated sample; and

FIG. 4 is a pictorial view of a typical concentrating apparatus for airborne pathogens.

DESCRIPTION OF THE PREFERRED EMBODIMENTS

As best shown in FIG. 1, a simple field kit for concentrating and detecting pathogens from water samples consists of a plastic trough 12 with two plastic skimming bars 14 and 15 and a reservoir 16 having a valve 17 for dropwise emptying the reservoir 16. For water sampling, a large volume (usually a gallon, or more) is used. A small amount of the sample is either poured into the trough 12 or valve 17 is opened to permit a more rapid flow until the bottom of trough 12 is covered. The remainder of the sample is applied dropwise to the surface of the sample present in the trough 12 by using a glass slide 18. The dropwise distribution of the sample from reservoir 16 results in a separation of the biological and organic phase, which localizes in a film 20 at the air/water interface, from the bulk water phase. Periodic draining of the accumulating bulk liquid allows the use of conveniently small troughs 12. After the formation of the initial surface monolayer of film 20, ordinarily taking place with the first few drops of solution, biological organisms (e.g. pathogens) concentrate at the interface with little or no alteration; there, with plenty of nearby nutrients, they thrive and multiply throughout the sampling period.

After sufficient interfacial film 20 is collected, which will be determined by the "richness" of the water sample (time may vary from minutes to hours), as shown in FIG. 2, and confining barriers defined by skimming bars 14 and 15 are moved together to compress the film 20 into a small area. Recovery of the compressed film 20 may be achieved by simply plucking it from the water surface with tweezers or, more efficiently, by passing a small plastic strip 22 through the interface between skimming bars 14 and 15 as shown in FIG. 3. The recovered film, still wet and biologically active, will continue to increase in concentration of living organisms during any storage period preceding testing for their presence. The surface concentration process will normally be more than adequate for producing a sample which can be tested immediately, in the field, with standard microbiological stains.

Air sampling can be achieved with the apparatus of FIG. 4. The worker would select a reasonably level area upon which to set the shallow plastic trough or tray 112. The trough 112 would then be nearly filled with any available water although uncontaminated water is preferred. A water sample would be saved for background analysis if it were suspected to be contaminated itself. Eyedropper 117 would then be used to gently add one drop of protein solution to the surface of the water to form film 120. No further operation would be necessary until sample retrievel was desired; however, if desired, fan 130, or the like, can be used to produce an increased air circulation. Sample retrievel would be essentially the same as in the case of water sampling. Plastic skimming bars or barriers 114 and 115 would be used to skim the film 120 and to concentrate the film 120 into a small area in the center of the trough 112. An inert plastic rod (not illustrated) will then be dragged through the concentrated film 120. The plastic rod with adhering sample would then be dropped wet into an empty vial, capped, and stored for delivery to a laboratory or used for immediate field testing.

The air sampling procedure depends upon the fact that small amounts of protein will spread at the air/water interface to cover very large surface areas (typically one square meter per milligram of protein spread). The resultant films may be nearly quantitatively recovered, with all that has fallen upon them and multiplied therein, by simple skimming, as described above. Protein films formed in this manner are excellent substrates for the growth and multiplication of airborne organisms which contact the film. The water substrate and multiple types of amino acids readily available encourage rapid, but local, bacteria proliferation.

The described procedure is sufficient for the setting of numerous air samplers which would work as "monomolecular flypapers", with the added advantages that sample multiplication would be occurring concurrently with collection and the final sample is obtained with a very high organism/collection medium ratio and small physical size. Although preferred embodiments of the present invention have been described, other changes will occur to those skilled in the art. It is therefore intended that the scope of the present invention is to be limited only by the scope of the appended claims.

I claim:

1. A method for detecting and concentrating airborne and waterborne pathogens including the steps of:
   providing an air/water interface having a relatively large surface area;
   contacting the air/water interface with the fluid to be tested so as to minimize agitation of the air/water interface;
   after a sufficient time, reducing the area of the air/water interface so as to concentrate pathogens collected at the air/water interface into a concentrate; and
   removing the concentrate from the air/water interface for analysis.

2. A method for detecting and concentrating airborne pathogens including the steps of:
   covering the bottom of a shallow receptacle with water;
   gently adding one drop of protein solution to the surface of the water to form a film at the air/water interface;
   after a sufficient time, reducing the area of the air/water interface so as to concentrate pathogens collected on the film at the air/water interface into a concentrate; and
   removing the concentrate from the receptacle for analysis.

3. A method for detecting and concentrating waterborne pathogens including the steps of:
   obtaining a sample of water to be tested;
   covering the bottom of a shallow receptacle with a small portion of the sample;
   applying the remainder of the sample dropwise to the air/water interface of the sample present in the receptacle;
   when sufficient sample has been added dropwise to the air/water interface, reducing the area of the air/water interface so as to concentrate pathogens collected on a film which forms at the air/water interface into a concentrate; and
   removing the concentrate from the receptacle for analysis.

* * * * *